(12) United States Patent
Knevels et al.

(10) Patent No.: US 6,855,238 B2
(45) Date of Patent: Feb. 15, 2005

(54) MEASURING DEVICE FOR DETERMINING THE OXYGEN ACTIVITY IN METAL MELTS OR SLAG MELTS

(75) Inventors: Johan Knevels, Bree (BE); Frank Mingneau, Zonhoven (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 10/056,919

(22) Filed: Jan. 25, 2002

(65) Prior Publication Data

US 2002/0100686 A1 Aug. 1, 2002

(30) Foreign Application Priority Data

Jan. 26, 2001 (DE) .......................... 101 03 701

(51) Int. Cl.[7] .............................. G01N 27/411
(52) U.S. Cl. ...................... 204/422; 204/424
(58) Field of Search ................ 204/421–429

(56) References Cited

U.S. PATENT DOCUMENTS

| | | | | |
|---|---|---|---|---|
| 3,410,778 A | * | 11/1968 | Kraserg | |
| 3,655,546 A | * | 4/1972 | Marovich et al. | |
| 3,752,753 A | * | 8/1973 | Fitterer | |
| 3,755,125 A | * | 8/1973 | Shaw et al. | |
| 3,809,639 A | * | 5/1974 | Faurschow et al. | |
| 3,959,107 A | * | 5/1976 | Horner et al. | |
| 4,105,507 A | * | 8/1978 | VonKrusenstierna et al. | |
| 4,342,633 A | * | 8/1982 | Cure | |
| 4,390,406 A | * | 6/1983 | Kato et al. | |
| 4,400,258 A | * | 8/1983 | Hans-Jurgen et al. | |
| 4,425,918 A | * | 1/1984 | Moll et al. | |
| 5,395,507 A | * | 3/1995 | Aston et al. | |
| 5,591,894 A | | 1/1997 | Falk et al. | |

FOREIGN PATENT DOCUMENTS

| | | |
|---|---|---|
| DE | 28 42 136 A1 | 10/1979 |
| DE | 3021949 A1 | 12/1981 |
| EP | 0 544 281 A1 | 6/1993 |
| FR | 2122758 * | 9/1972 |
| GB | 1 473 761 | 5/1977 |
| GB | 1 550 783 | 8/1979 |

OTHER PUBLICATIONS

Abstract for JP 06258282, Sep. 1994.

* cited by examiner

*Primary Examiner*—Kaj K. Olsen
(74) *Attorney, Agent, or Firm*—Akin Gump Strauss Hauer & Feld, LLP

(57) ABSTRACT

A measuring device for determining the oxygen activity in metal melts or slag melts has a measuring head arranged on the end of a carrier tube, on which head an electrochemical measuring cell is arranged. The electrochemical measuring cell has a solid electrolyte tube closed on one end, which is surrounded on the closed end and at least on a portion of its periphery by a steel tube closed on one end. A reference material and a filler material adjoining the reference material are arranged inside the solid electrolyte tube on its closed end. A metal rod is arranged as an electrode along the solid electrolyte tube in such a manner that, on the one hand, it stands in contact with the reference material and, on the other hand, it projects out of the open end of the solid electrolyte tube. The open end of the solid electrolyte tube has a closure which is constructed as a cap, which fits on the exterior of the steel tube or the solid electrolyte tube, and the closure is gas-permeable.

12 Claims, 2 Drawing Sheets

MEASURING DEVICE FOR DETERMINING THE OXYGEN ACTIVITY IN METAL MELTS OR SLAG MELTS

BACKGROUND OF THE INVENTION

The invention relates to a measuring device for determining the oxygen activity in metal melts, especially iron, steel or cast iron melts, or slag melts, with a measuring head arranged on the end of a carrier tube, on which an electrochemical measuring cell is arranged, wherein the electrochemical measuring cell has solid electrolyte tube closed on one end, which is surrounded on the closed end and at least on a portion of its periphery by a steel tube closed on one end, wherein a reference material and a filler material adjoining the reference material are arranged inside the solid electrolyte tube on its closed end, wherein a metal rod is arranged as an electrode along the solid electrolyte tube in such a manner that, on the one hand, it stands in contact with the reference material and, on the other hand, it projects out of the open end of the solid electrolyte tube, and wherein the open end of the solid electrolyte tube has a closure.

A measuring device of this type is known from German published patent application DE 30 21 949 A1. This measuring device has a solid electrolyte tube, which is closed gas-tight on its open end by a rubber stopper. The rubber stopper extends into the solid electrolyte tube and is pressed against its inner wall, whereby the degree of sealing depends, among other things, on the size of the contact surface on the solid electrolyte tube. During the measuring process, this device is dipped into a steel melt. There then follows a very rapid and extreme temperature change. Due to the gases confined in the interior of the solid electrolyte tube, the internal pressure is thereby considerably increased, so that particular requirements must be placed on the strength of the solid electrolyte tube or its metal casing.

To solve a similar problem with a quartz glass tube, it is proposed in British patent specification GB 1 473 761 to guide gases from an inert material outside through a vent tube. A further measuring device for determining the oxygen activity of metal melts is described in German published patent application DE 28 42 136 A1.

BRIEF SUMMARY OF THE INVENTION

Underlying the invention is the objective of improving the known solution of the prior art. According to the invention, the objective is accomplished by constructing the closure as a cap, which fits on the exterior of the steel tube or the solid electrolyte tube, and the closure being gas-permeable. Owing to the fact that the closure is constructed as a cap fitting on the exterior of the steel tube or the solid electrolyte tube, the gas permeability of the closure provided in accordance with the invention can be developed without stresses, so that an overall defined gas penetration profile can be guaranteed in the closure.

Preferably, the closure has openings. The openings are arranged in the region of the open end of the solid electrolyte tube, so that a gas exchange can take place between the interior of the solid electrolyte tube and its surroundings. In this way, a pressure increase during temperature change in the interior of the solid electrolyte tube is at least substantially avoided, and at the same time a penetration of moisture into the interior of the electrochemical element is prevented. For this purpose, the openings are limited in their size.

It has proven to be expedient to construct the closure as a plastic cap, especially of polypropylene. Plastics have an elasticity, which permits a close fit on the exterior of the solid electrolyte tube or the steel tube. The plastic cap is preferably fixed on the steel tube or the solid electrolyte tube by means of a snap lock, that is, by using latching elements. In its center the closure has a bushing, which prior to assembly has a somewhat smaller diameter than the electrode, which is inserted through it. In this manner, a tightly sealing fit of the closure on the electrode with stretching is guaranteed. Expediently, the closure also fits liquid-tight on the steel tube or the solid electrolyte, especially with stretching. The closure can be porous, in order to be gas-permeable.

Preferably, several openings in the closure, particularly three to five openings, are uniformly arranged around the longitudinal axis of the solid electrolyte tube. The openings are preferably arranged in a planar part of the closure oriented approximately perpendicular to the axis of the solid electrolyte tube. The closure preferably has a tube-shaped segment, which fits closely on the electrode. Between the tube-shaped segment and the segment of the closure fitting on the exterior of the steel tube or the solid electrolyte tube, a conical segment is expediently arranged. In addition, or alternatively, openings can be arranged on the conical segment.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
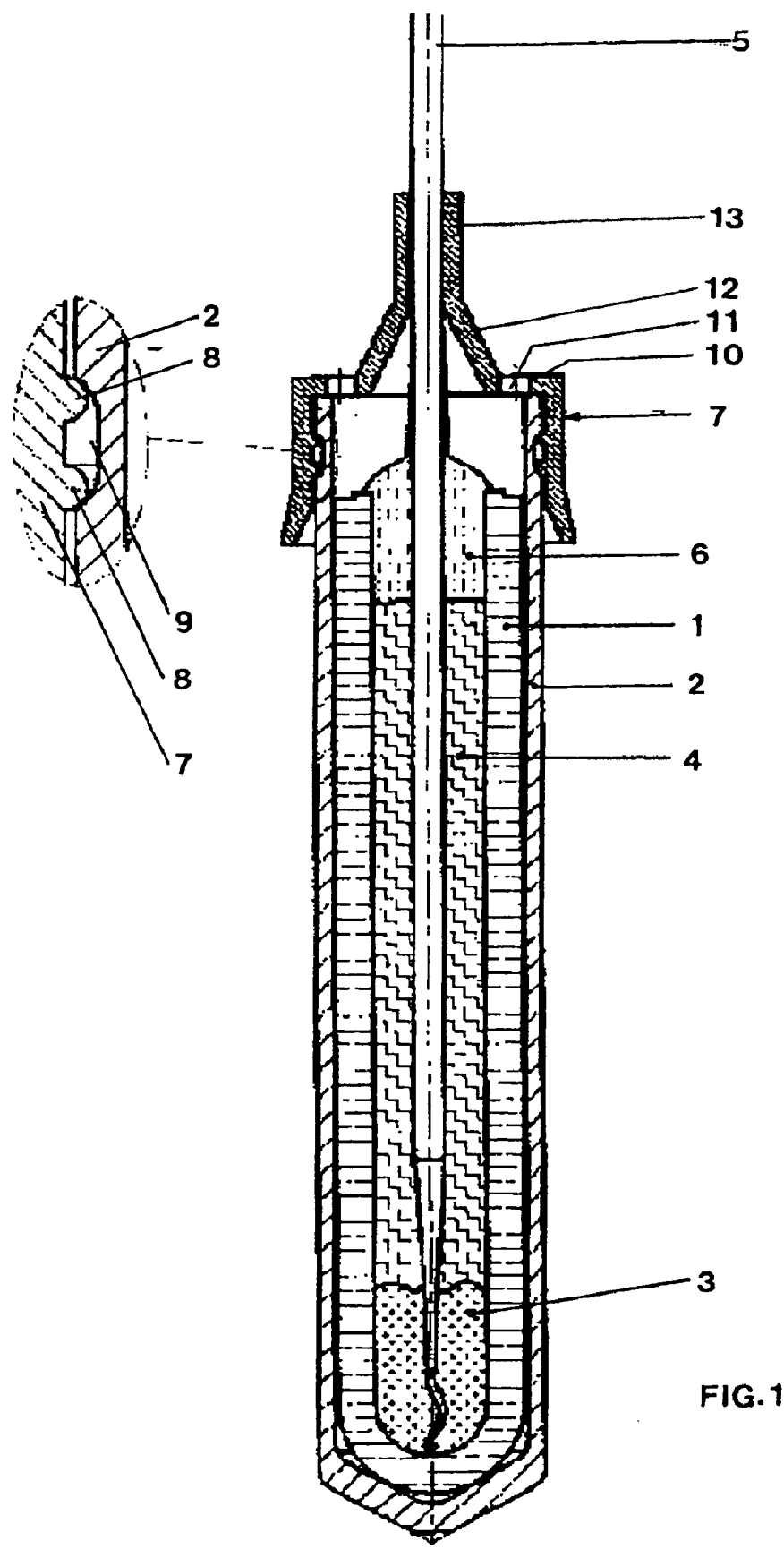
FIG. 1 is a cross-section through the measuring cell of the invention with a detail representation of the latching device.

The electrochemical measuring cell shown in FIG. 1 is arranged in measuring heads described, for example, in German published patent applications DE 30 21 949 A1 or DE 28 42 136 A1. The measuring heads are held by support tubes in a known manner.

The solid electrolyte tube 1, made of zirconium dioxide, is closed on one end and surrounded by a closed steel tube 2, likewise closed on one end (the immersion end). In the closed tip of the solid electrolyte tube 1, a mixture of chromium and chromium dioxide is arranged as a reference material 3. The filler material 4 arranged above the reference material is, for example, aluminum oxide. Above the filler material 4, a gas-permeable cement 6 is arranged, which closes the open area of the solid electrolyte tube 1. In the solid electrolyte tube 1 a molybdenum rod is arranged centrally as an electrode 5.

The open end of the steel tube is closed with a plastic cap 7 made of polypropylene. The plastic cap 7 fits closely on the exterior of the steel tube 2 with stretching and is there fixed by means of latching nubs 8 inside a groove 9 in the exterior of the steel tube 2, although the nubs and groove could be reversed in position. Connected to the part of the plastic cap 7 fitting on the periphery of the steel tube 2 is a segment 10, oriented perpendicular to the axis of the solid electrolyte tube, in which openings 11 are arranged. This planar segment 10 is bounded toward the electrode 5 by a conical segment 12, which connects with a tube-shaped segment 13. This tube-shaped segment 13 has a central bushing which fits closely on electrode 5. In the disassembled state the bushing of the tube-shaped segment 13 is slightly smaller than the cross-section of the electrode 5. During assembly, the tube-shaped segment 13 is expanded and then fits with tightening on the electrode 5.

Figure 2:
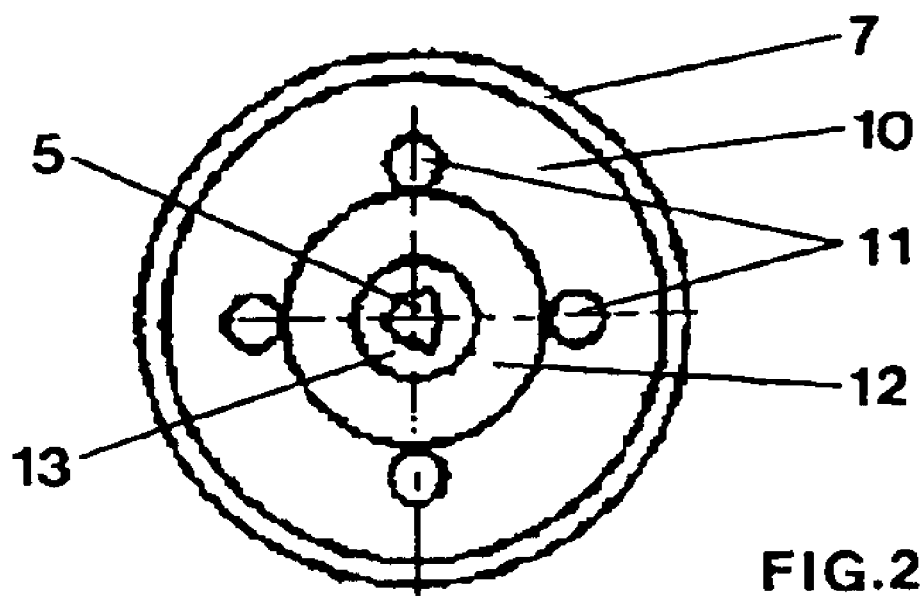
FIG. 2 is a plan view of the measuring cell of FIG. 1.

As shown in FIG. 2, the openings 11 are evenly distributed around the electrode 5. In total, four of the openings 11 are provided with a cross-section in all cases slightly larger than 0.01 mm$^2$.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A measuring device for determining oxygen activity in metal melts or slag melts, comprising a measuring head arranged on one end of a carrier tube, an electrochemical measuring cell being arranged on the measuring head, wherein the electrochemical measuring cell has a solid electrolyte tube (1) closed on one end and open on an opposite end, the solid electrolyte tube being surrounded on the closed end and at least on a portion of its periphery by a steel tube (2) closed on one end, wherein a reference material (3) and a filler material (4) adjoining the reference material are arranged inside the solid electrolyte tube at its closed end, wherein a metal rod is arranged as an electrode (5) along the solid electrolyte tube in such a manner that the metal rod stands in contact with the reference material and projects out of the open end of the solid electrolyte tube, wherein the open end of the solid electrolyte tube has a closure, and wherein the closure (7) is constructed as a cap, which fits on an exterior of the steel tube (2) or the solid electrolyte tube (1), and the closure (7) is gas-permeable and comprises polypropylene.

2. The measuring device according to claim 1, wherein the closure (7) has openings (11) for gas-permeable connection of an interior of the solid electrolyte tube (1) with its surroundings.

3. The measuring device according to claim 2, wherein the openings (11) each have a cross-sectional area of at least 0.01 mm2.

4. The measuring device according to claim 2, wherein the openings (11) are evenly distributed around a longitudinal axis of the solid electrolyte tube (1).

5. The measuring device according to claim 4, wherein the closure has three to five of the openings (11).

6. The measuring device according to claim 1, wherein the closure (7) is fixed liquid-tight on the exterior of the steel tube (2) or the solid electrolyte tube (1).

7. The measuring device according to claim 1, wherein the closure (7) is fixed by latching devices (8; 9) on the exterior of the steel tube (2) or the solid electrolyte tube (1).

8. The measuring device according to claim 1, wherein the closure (7) has a central bushing which encloses the electrode (5).

9. The measuring device according to claim 8, wherein the closure (7) has a tube-shaped segment (13) in which the bushing is arranged, the tube-shaped segment extending along the electrode (5) and tightly enclosing the electrode (5).

10. The measuring device according to claim 8, wherein the closure (7) has a conical segment (12) between the bushing and a segment fitting on the exterior of the steel tube (2) or the solid electrolyte tube (1).

11. The measuring device according to claim 10, wherein the segment of the closure (7) fitting on the exterior of the steel tube (2) or the solid electrolyte tube (1) has a planar segment (10) arranged over the open end of the solid electrolyte tube (1) and oriented perpendicular to a longitudinal axis of the solid electrolyte tube (1).

12. The measuring device according to claim 11, wherein the closure (7) has openings (11) for gas-permeable connection of an interior of the solid electrolyte tube (1) with its surroundings and the openings (11) are arranged in the planar segment (10).

* * * * *